United States Patent [19]

Sapino

[11] Patent Number: 6,096,760
[45] Date of Patent: Aug. 1, 2000

[54] SOLID α-PHENYL-2-PIPERIDINE ACETATE FREE BASE, ITS PREPARATION AND USE IN MEDICINE

[75] Inventor: Chester Sapino, Sewell, N.J.

[73] Assignee: Johnson Matthey Public Limited Company, London, United Kingdom

[21] Appl. No.: 09/086,727

[22] Filed: May 29, 1998

[30] Foreign Application Priority Data

May 30, 1997 [GB] United Kingdom ............... 9711032

[51] Int. Cl.$^7$ .................. A61K 31/445; C07D 211/26
[52] U.S. Cl. .................. 514/317; 514/331; 546/233
[58] Field of Search ................. 514/317, 331; 546/233

[56] References Cited

U.S. PATENT DOCUMENTS

| | | | |
|---|---|---|---|
| 2,507,631 | 5/1950 | Hartmann et al. | 546/233 |
| 2,838,519 | 6/1958 | Rometsch | 546/233 |
| 2,957,880 | 10/1960 | Rometsch | 546/233 |
| 4,201,211 | 5/1980 | Chandrasekaran | 128/268 |
| 4,293,565 | 10/1981 | Cordes | 514/470 |
| 4,322,433 | 3/1982 | Keskue | 514/509 |
| 4,341,208 | 7/1982 | Gordon | 604/307 |
| 4,379,454 | 4/1983 | Campbell | 604/897 |
| 4,559,222 | 12/1985 | Enscore | 424/486 |
| 4,685,911 | 8/1987 | Konno | 604/897 |
| 4,752,478 | 6/1988 | Bondi | 424/486 |
| 5,318,960 | 6/1994 | Toppo | 514/159 |

FOREIGN PATENT DOCUMENTS

| | | |
|---|---|---|
| 269338 | 11/1950 | Switzerland . |
| 269656 | 11/1950 | Switzerland . |
| 589625 | 11/1947 | United Kingdom . |

OTHER PUBLICATIONS

Kolbina "Identification of methyl alpha–phenyl–2–piperidylacetate" CA 101:203680, 1984.

The Merck index, ninth edition, p. 5972, 1976.

*Primary Examiner*—Ceila Chang
*Attorney, Agent, or Firm*—Pillsbury Madison & Sutro LLP

[57] ABSTRACT

Methyl α-phenyl-2-piperidine acetate (free base) is disclosed as a crystalline solid, together with a method for its preparation; its use in medicine, in particular as a stimulant for the central nervous system; and pharmaceutical formulations comprising the compound, particularly transdermal patches.

10 Claims, No Drawings

SOLID α-PHENYL-2-PIPERIDINE ACETATE FREE BASE, ITS PREPARATION AND USE IN MEDICINE

The present invention relates to methyl α-phenyl-2-piperidine acetate free base in solid form, a method for its preparation, its use in medicine, in particular as a stimulant for the central nervous system, and pharmaceutical formulations thereof.

It is well known in the literature that methyl α-phenyl-2-piperidine acetate hydrochloride exerts a mild stimulating effect on the central nervous system, and can be used to overcome states of fatigue, depression and exhaustion, for instance in convalescence. It may also be used in combination with an antihistamine, for example with benzyldimethylaminoethylaminopyridine, to counteract allergies (see, for example, U.S. Pat. Nos. 2,838,519 and 2,957,880). Methyl α-phenyl-2-piperidine acetate hydrochloride is available under the trade name Ritalin.

However, the hydrochloride salt cannot be readily absorbed through the skin and is therefore not suitable for use in formulations for transdermal use, such as transdermal patches. For such uses, it would be preferable to use a free base rather than the hydrochloride salt. However, all the disclosures in the literature describing the synthesis of the free base refer to an oil with a boiling point of 135–137° C. under 0.6 mm pressure (see, for example, GB 589,625; U.S. Pat. No. 2,507,631; CH 269 338 and CH 269 656), which is therefore unsuitable for use in formulations requiring a solid form, such as transdermal patches. There is no previous reference to a method for synthesising the free base as a solid.

The present inventors have devised a synthetic route which results in producing the free base as a solid. Accordingly, the present invention provides methyl α-phenyl-2-piperidine acetate (free base) in solid form. More particularly, the present invention provides methyl α-phenyl-2-piperidine acetate (free base) in solid crystalline form.

A further aspect of the present invention relates to a process for preparing methyl-α-phenyl-2-piperidine acetate (free base), which process comprises:
(i) dissolving a salt of methyl α-phenyl-2-piperidine acetate in a mixture of a suitable organic solvent and an aqueous base; and
(ii) evaporating the organic solution from the aqueous solution thereby formed, whereby an oil is formed that solidifies on standing to form crude solid free base.

Any salt of methyl α-phenyl-2-piperidine acetate may be used in this process. For example, salts of organic acids, such as the maleate salt, or salts of inorganic acids, such as the hydrochloride or sulphate, or the like. However, the most readily available salt is the hydrochloride and this is therefore preferred for use in the process according to the present invention.

Any organic solvent in which the salt dissolves and from which the solid free base can be obtained may be used, but non-polar organic solvents are preferred. Particularly preferred are alkanes such as straight chain $C_{1-8}$ alkanes. Especially preferred is heptane.

Any aqueous base which is strong enough to deprotonate the piperidine may be used. Preferred inorganic bases are alkali or alkaline earth metal hydroxides or carbonates, such as NaOH, $Na_2CO_3$, or their potassium or lithium analogues. Particularly preferred is sodium hydroxide (NaOH).

A preferred process according to the present invention is one which further comprises:

(iii) dissolving the crude solid, obtained from steps (i) to (ii), in an organic solvent and recrystallising the free base therefrom.

The preferred organic solvent for this step (iii) is 2,2,4-trimethylpentane. Preferably, the recrystallisation is effected by cooling the organic solution to less than 10° C. and seeding the solution with crude solid, more preferably with stirring.

A particularly preferred process according to this invention therefore comprises preparing methyl α-phenyl-2-piperidine acetate free base in solid crystalline form, said process comprising the steps of:
(i) stirring the hydrochloride salt in a suitable organic solvent and aqueous base;
(ii) evaporating the solvent from the organic layer to leave an oil that solidifies on standing to produce a crude solid;
(iii) dissolving the crude solid in an organic solvent, cooling to less than 10° C. and seeding with crude solid whilst continuing stirring.

Especially preferred is a process comprising:
(i) stirring methyl α-phenyl-2-piperidine acetate hydrochloride in heptane and an aqueous inorganic base, such as an alkali or alkaline earth metal hydroxide or carbonate;
(ii) evaporating the solvent from the organic layer to leave an oil that solidifies on standing; and, optionally but more preferably;
(iii) dissolving the crude solid in 2,2,4-trimethyl pentane, and seeding with crude solid at below 10° C. with stirring.

A preferred temperature range for the recrystallisation step (iii) is from about 3° to about 8° C. More preferably, the solution is seeded at from about 8° to about 10° C. and the temperature reduced further to from about 2° to about 4° C. during stirring. The crystalline solid thereby produced may be filtered with further 2,2,4-trimethylpentane and thereafter dried, preferably under vacuum in an inert atmosphere such as nitrogen.

Due to the problems associated with formulating an oil into certain pharmaceutical compositions, a salt, in particular the hydrochloride salt, not the free base, has always been used in medicine. Since the present inventors have devised a method for preparing a solid form of the free base, it is possible for the first time to formulate solid pharmaceutical compositions from the free base. Accordingly, the present invention further provides methyl α-phenyl-2-piperidine acetate (free base) in solid form for use in medicine, in particular for use in stimulating the central nervous system. A still further aspect of the present invention provides the use of methyl α-phenyl-2-piperidine acetate (free base) in solid form in the manufacture of a medicament for treating conditions requiring stimulation of the central nervous system. Specifically, methyl α-phenyl-2-piperidine acetate (free base) can be used in cases of attention deficit disorder in both adults and children.

Whilst it may be possible for methyl α-phenyl-2-piperidine acetate (free base) to be administered as the raw chemical, it is preferable to present it as a pharmaceutical formulation. According to a further aspect, the present invention provides a pharmaceutical formulation comprising methyl α-phenyl-2-piperidine acetate (free base) in solid form together with a pharmaceutically acceptable carrier therefor and optionally other therapeutic ingredient(s). The carrier(s) must be "acceptable" in the sense of being compatible with the other ingredients of the formulation and not deleterious to the recipient thereof.

The formulations include those suitable for oral, parenteral (including subcutaneous, intradermal, intramuscular, intravenous and intra-articular), and topical (including dermal, buccal, sublingual and intraocular) administration, although the most suitable route may depend upon, for example, the condition and disorder of the recipient. The formulations may conveniently be presented in unit dosage form and may be prepared by any of the methods well known in the art of pharmacy. All methods include the step of bringing into association the free base in solid form with the carrier.

In general, the formulations are prepared by uniformly and intimately bringing into association the free base in solid form with liquid carriers or finely divided solid carriers or both and then, if necessary, shaping the product into the desired formulation.

In particular, the present invention provides a formulation suitable for transdermal administration of methyl α-phenyl-2-piperidine, which formulation comprises a substrate adapted to remain during treatment on the skin and methyl α-phenyl-2-piperidine (free base) in solid form. The present invention further provides a transdermal patch comprising methyl α-phenyl-2-piperidine (free base) in crystalline solid form.

The present invention will now be illustrated by way of Example only.

EXAMPLE

PREPARATION AND ANALYSIS OF CRYSTALLINE SOLID FREE BASE

Methyl α-phenyl-2-piperidine acetate hydrochloride (70.89 g, 0.263 mole) was stirred in a mixture of heptane (500 ml) and 10% NaOH (250 ml, 0.63 mole) for 20 minutes until there was no solid present. The solutions were allowed to separate. The upper heptane layer was saved and the lower aqueous layer was back-extracted with heptane (100 ml). The combined heptane layers were dried over $Na_2SO_4$ (50 g) and molecular sieves (3A, 10 g) for 1 hour. The solution was filtered and concentrated in vacuo on the rotary evaporator to an oil. The oil was dried on the rotary evaporator (4 hours/55° C./5 mm Hg). The oil solidified on standing overnight at room temperature.

The above crude solid (54.28 g) was dissolved in 2,2,4-trimethylpentane (150 ml) with gentle warming and filtered through a 0.2μ filter with a fresh 2,2,4-trimethylpentane (65 ml) rinse. The solution was stirred on an ice bath. When the solution reached 8° C. it was seeded with solid crude methyl α-phenyl-2-piperidine acetate. The mixture was stirred at 3° C. for 1.5 hours. The solid which formed was filtered with a cold fresh 2,2,4-trimethylpentane (65 ml) rinse. The solid was blown dry under $N_2$ on the filter for 2 hours giving a first crop of methyl α-phenyl-2-piperidine acetate (free base). The filtrate was stirred at 3° C. for 1 hour and the second crop was filtered. The solid was blown dry under $N_2$ on the filter for 2 hours giving a second crop of methyl α-phenyl-2-piperidine acetate free base. The combined solids were dried at room temperature in the vacuum over for 15 hours giving methyl α-phenyl-2-piperidine acetate (free base) as white solid and their melting point (measured on a Thomas Hoover Capillary Melting Point Apparatus) was found to be 41°–42° C. Elemental analysis calculated for $C_{14}H_{19}NO_2$: theory: C, 72.07; H 8.21; N, 6.00; found: C, 72.17; H, 7.95; N, 6.03.

$^1$H NMR (CDCl$_3$) δ7.22–7.38 (m, 5H, phenyl), 3.63 (s, 3H, —CO$_2$CH$_3$), 3.44 (d(J=11 Hz), 1H, —CH—(Ph) CO$_2$Me), 3.06–3.25 (m, 2H, —CH—CH(Ph)CO$_2$Me and —CH$_{(e)}$NCH—CH(Ph)—(CO$_2$Me)), 2.70 (dt(J=4, 12 Hz), 1H, —CH$_{(a)}$NCH—CH(Ph)(CO$_2$Me)), 1.90 (bs, 1H, NH), 0.88–1.78 (m, 6H, —CH$_2$—CH$_2$—CH$_2$—).

We claim:

1. The compound methyl α-phenyl-2-piperidine acetate free base, in solid form and having a melting point of 41–42° C.

2. The compound of claim 1, in crystalline form.

3. A method of stimulating the central nervous system in a patient in need thereof, which method comprises the administration to the patient of a therapeutically effective amount of a compound according to claim 1 or claim 2.

4. A pharmaceutical formulation comprising a compound according to claim 1 or claim 2, together with a pharmaceutically acceptable carrier therefor.

5. A pharmaceutical formulation comprising a compound according to claim 1 or claim 2 in a form selected from those suitable for topical and transdermal administration.

6. A transdermal patch, comprising a compound according to claim 1 or claim 2.

7. A process for preparing a compound according to claim 1 or claim 2, which process comprises the steps of:
 (i) dissolving a salt of methyl α-phenyl-2-piperidine acetate hydrochloride in a mixture of a suitable organic solvent and an aqueous base; and
 (ii) evaporating the organic solution from the aqueous solution thereby formed, whereby an oil is formed that solidifies on standing to form crude solid free base.

8. A process for preparing a compound according to claim 1 or claim 2, which process comprises the steps of:
 (i) dissolving a salt of methyl α-phenyl-2-piperidine acetate hydrochloride in a mixture of a suitable organic solvent and an aqueous base;
 (ii) evaporating the organic solution from the aqueous solution thereby formed, whereby an oil is formed that solidifies on standing to form crude solid free base, dissolving the crude solid, obtained from steps (i) to (ii), in an organic solvent and recrystallising the free base therefrom; and
 (iii) dissolving the crude solid, obtained from steps (i) to (ii), in an organic solvent and recrystallising the free base therefrom.

9. A process for preparing methyl α-phenyl-2-piperidine acetate (free base), which process comprises the steps of:
 (i) stirring methyl α-phenyl-2-piperidine acetate hydrochloride in a suitable organic solvent and aqueous base;
 (ii) evaporating the organic layer to leave an oil which solidifies on standing; and
 (iii) dissolving the crude solid in an organic solvent, cooling to less than 10° C. and seeding with crude solid whilst continuing stirring.

10. A process according to claim 9, which process comprises:
 (i) stirring methyl α-phenyl-2-piperidine acetate hydrochloride in heptane and an aqueous inorganic base, such as an alkali or alkaline earth metal hydroxide or carbonate;
 (ii) evaporating the solvent from the organic layer to leave an oil that solidifies on standing; and, optionally,
 (iii) dissolving the crude solid in 2,2,4-trimethylpentane, and seeding with crude solid at below 10° C. with stirring.

* * * * *